United States Patent
Shekhar et al.

(10) Patent No.: US 10,202,318 B2
(45) Date of Patent: Feb. 12, 2019

(54) CATALYST AND ITS USE IN HYDROCARBON CONVERSION PROCESS

(71) Applicant: ExxonMobil Chemical Patents Inc., Baytown, TX (US)

(72) Inventors: Mayank Shekhar, Houston, TX (US); Paul F. Keusenkothen, Houston, TX (US); Machteld M. W. Mertens, Boortmeerbeek (BE); Anthony Go, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/240,622

(22) Filed: Aug. 18, 2016

(65) Prior Publication Data
US 2017/0088485 A1    Mar. 30, 2017

Related U.S. Application Data

(60) Provisional application No. 62/299,730, filed on Feb. 25, 2016, provisional application No. 62/232,609, filed on Sep. 25, 2015.

(30) Foreign Application Priority Data

Nov. 19, 2015  (EP) ..................................... 15195311
Apr. 28, 2016  (EP) ..................................... 16167395

(51) Int. Cl.
C07C 2/76 (2006.01)
B01J 37/08 (2006.01)
B01J 29/40 (2006.01)

(52) U.S. Cl.
CPC .............. *C07C 2/76* (2013.01); *B01J 29/405* (2013.01); *B01J 37/08* (2013.01); *B01J 2229/18* (2013.01); *B01J 2229/32* (2013.01); *C07C 2529/40* (2013.01)

(58) Field of Classification Search
None
See application file for complete search history.

(56) References Cited

U.S. PATENT DOCUMENTS

| | | |
|---|---|---|
| 3,354,078 A | 11/1967 | Miale et al. |
| 3,702,886 A | 11/1972 | Argauer et al. |
| 3,709,979 A | 1/1973 | Chu |
| 3,766,093 A | 10/1973 | Chu |
| 3,832,449 A | 8/1974 | Rosinski et al. |
| 3,894,104 A | 7/1975 | Chang et al. |
| 3,960,978 A | 6/1976 | Givens et al. |
| 3,972,832 A | 8/1976 | Butter et al. |
| 4,016,218 A | 4/1977 | Haag et al. |
| 4,016,245 A | 4/1977 | Plank et al. |
| 4,021,502 A | 5/1977 | Plank et al. |
| 4,046,859 A | 9/1977 | Plank et al. |
| 4,076,842 A | 2/1978 | Plank et al. |
| 4,082,805 A | 4/1978 | Kaeding |
| RE29,948 E | 3/1979 | Dwyer et al. |
| 4,150,062 A | 4/1979 | Garwood et al. |
| 4,227,992 A | 10/1980 | Garwood et al. |
| 4,229,424 A | 10/1980 | Kokotailo |
| 4,234,231 A | 11/1980 | Yan |
| 4,439,409 A | 3/1984 | Puppe et al. |
| 4,456,781 A | 6/1984 | Marsh et al. |
| 4,556,477 A | 12/1985 | Dwyer |
| 4,640,826 A | 2/1987 | Williams et al. |
| 4,826,667 A | 5/1989 | Zones et al. |
| 4,873,067 A | 10/1989 | Valyocsik et al. |
| 4,954,325 A | 9/1990 | Rubin et al. |
| 5,026,937 A * | 6/1991 | Bricker ..................... C07C 2/76 585/415 |
| 5,236,575 A | 8/1993 | Bennett et al. |
| 5,250,277 A | 10/1993 | Kresge et al. |
| 5,362,697 A | 11/1994 | Fung et al. |
| 5,574,199 A | 11/1996 | Beck et al. |
| 5,990,032 A * | 11/1999 | Wu ....................... B01J 29/061 502/60 |
| 5,998,686 A | 12/1999 | Clem et al. |
| 6,049,018 A | 4/2000 | Calabro et al. |
| 6,074,975 A | 6/2000 | Yao et al. |
| 6,077,498 A | 6/2000 | Diaz Cabanas et al. |
| 6,670,517 B1 | 12/2003 | Abichandani et al. |
| 6,756,030 B1 | 6/2004 | Rohde et al. |
| 7,713,513 B2 | 5/2010 | Jan et al. |
| 8,835,706 B2 | 9/2014 | Iyer et al. |
| 2006/0182681 A1* | 8/2006 | Kumar ................... B01J 29/005 423/700 |
| 2009/0209794 A1 | 8/2009 | Lauritzen et al. |

FOREIGN PATENT DOCUMENTS

| | | |
|---|---|---|
| EP | 0 293 032 | 11/1988 |
| WO | 97/17290 | 5/1997 |
| WO | 2010/140005 | 12/2010 |

OTHER PUBLICATIONS

Baerlocher et al., "*Atlas of Zeolite Framework Types*", Fifth Revised Edition, 2001.
Miale et al., "Catalysis by Crystalline Aluminosilicates—IV. Attainable Catalytic Cracking Rate Constants, and Superactivity", Journal of Catalysis, 1966, vol. 6, pp. 278-287.
Olson et al., "Chemical and Physical Properties of the ZSM—5 Substitutional Series", Journal of Catalysis, 1980, vol. 61, pp. 390-396.
Weisz et al., "Superactive Crystalline Aluminosilicate Hydrocarbon Catalysts", Journal of Catalysis, 1965, vol. 4, pp. 527-529.
Huayun Long, et al: "Effect of lanthanum and phosphorus on the aromatization activity of Zn/ZSm—5 in FCC gasoline upgrading", Microporous and Mesoporous Materials, vol. 198, Jul. 19, 2014, pp. 29-34.

\* cited by examiner

*Primary Examiner* — Tam M Nguyen

(57) ABSTRACT

The invention relates to catalysts and their use in processes for conversion of hydrocarbon feedstock to a product comprising single-ring aromatic hydrocarbons having six or more carbon atoms, to the methods of making such catalysts, to processes for using such catalysts, and to apparatus and systems for carrying out such processes. One of more of the catalysts comprise a crystalline aluminosilicate having a Constraint Index in the range of 1 to 12, a first metal and/or a second metal, and at least one selectivating agent, such as, for example, an organo-silicate.

6 Claims, No Drawings

CATALYST AND ITS USE IN HYDROCARBON CONVERSION PROCESS

CROSS-REFERENCE TO RELATED APPLICATIONS

This invention claims priority to and the benefit of U.S. Patent Application Ser. No. 62/299,730, filed Feb. 25, 2016, European Patent Application No. 16167395.9 filed Apr. 28, 2016, U.S. Patent Application No. 62/232,609, filed Sep. 25, 2015 and European Patent Application No. 15195311.4, filed Nov. 19, 2015, each being incorporated by reference in its entirety. The following related cases are also incorporated by reference in their entireties: U.S. Patent Application Ser. No. 62/234,262; European Patent Application No. 15195314.8; U.S. Patent Application Ser. No. 62/234,240; European Patent Application No. 15197698.2; U.S. Patent Application Ser. No. 62/247,795; European Patent Application No. 15197700.6; U.S. Patent Application Ser. No. 62/248,374; European Patent Application No. 15197702.2; U.S. Patent Application Ser. No. 62/253,268; U.S. Patent Application Ser. No. 62/298,655; European Patent Application No. 16167672.1; U.S. Patent Application Ser. No. 62/326,918; European Patent Application No. 16175163.1; U.S. Patent Application Ser. No. 62/313,288, European Patent Application No. 16173587.3; U.S. Patent Application Ser. No. 62/313,306 and European Patent Application No. 16173980.0.

FIELD

The invention relates to catalysts, preferably selectivated catalysts, and their use in processes for conversion of a hydrocarbon feedstock to a product comprising higher-value hydrocarbon. Preferably, the feedstock comprises one or more paraffinic light hydrocarbon compounds having no more than five carbon atoms, such as methane, ethane, propane and butane. The higher-value hydrocarbon preferably includes hydrocarbon having six or more carbon atoms, for example, aromatic hydrocarbon such as one or more benzene, toluene and mixed xylenes.

BACKGROUND

Aromatic hydrocarbon compounds such as benzene are frequently used for producing transportation fuels and petrochemicals such as styrene, phenol, nylon, polyurethanes, and many others. Benzene is typically produced in processes such as steam cracking and catalytic reforming. During steam cracking, a $C_{2+}$ hydrocarbon feedstock is exposed to high-temperature pyrolysis conditions to produce a product comprising molecular hydrogens, $C_{4-}$ olefin, other $C_{4-}$ hydrocarbons, and $C_{5+}$ hydrocarbons. The yield of aromatic hydrocarbon from steam cracking is generally much less than the yield of light hydrocarbon. Consequently, complex processes typically are needed for separating and recovering aromatic hydrocarbon from steam cracker effluent. Catalytic naphtha reforming produces a product having a much greater content of aromatic hydrocarbon than steam cracker effluent, but the naphtha feedstock is itself useful for other purposes such as a motor gasoline blendstock.

Various attempts have been made to provide an efficient process for producing aromatic hydrocarbon at high yield from a relatively inexpensive feedstock. For example, processes have been developed for producing light aromatic hydrocarbon (e.g., benzene, toluene, and mixed xylenes—"BTX") from paraffinic $C_{4-}$ feedstock. The processes typically utilize an acidic molecular sieve, such as ZSM-5, and at least one metal having dehydrogenation functionality, such as one or more of Pt, Ga, Zn, and Mo. These conventional processes typically operate at high temperature and low pressure. Although these conditions are desirable for producing aromatic hydrocarbon, they also lead to undue catalyst deactivation as a result of increased catalyst coking. Also, these conventional processes are not selective for the desirable single-ring aromatic hydrocarbons, such as benzene, toluene and xylene, and produce undesirably large amounts of multiple-ring aromatic hydrocarbons, such as naphthalene.

Therefore, a need exists for processes which convert relatively low-value hydrocarbon feedstock, particularly those processes exhibiting a greater reaction selectivity to the desirable single-ring aromatic hydrocarbon, a lesser reaction selectivity to the undesirable multiple-ring aromatic hydrocarbon, and an acceptable level of feedstock conversion. This invention meets this need and others.

SUMMARY

In one aspect, the invention is a catalyst, preferably a selectivated catalyst, that may be used in processes for converting a relatively low-value hydrocarbon feedstock, such as light paraffinic hydrocarbon feedstock, including those comprising one or more light hydrocarbon compounds having no more than five carbon atoms. The product formed comprises aromatic hydrocarbon, particularly one or more single-ring aromatic hydrocarbon compounds having six or more carbon atoms.

The catalyst comprises a crystalline aluminosilicate zeolite, optionally in hydrogen form having hydrogen ions, a Constraint Index in the range of 1 to 12, a first metal, and at least one selectivating agent. Optionally, the catalyst further comprises a second metal, wherein the second metal is different from the first metal. In one or more embodiments, the selectivating agent is selected from the group consisting of organo-silicate, an organo-aluminate, an organo-phosphate, and mixtures of two or more thereof. Preferably, the selectivating agent is tetraethyl orthosilicate (TEOS).

In certain aspects, the crystalline aluminosilicate zeolite which has a Constraint Index of 1 to 12 is selected from the group consisting of MCM-22 family materials, ZSM-5, ZSM-11, ZSM-12, ZSM-21, ZSM-22, ZSM-23, ZSM-35, ZSM-38, ZSM-48, ZSM-50, ZSM-57, MCM-68, and mixtures of two or more thereof. Preferably, such crystalline aluminosilicate zeolite is ZSM-5 or ZSM-11.

The first metal is selected from the group consisting of zinc, gallium, platinum, copper, rhenium, iron, and mixtures of two or more thereof; preferably, zinc and/or gallium. The second metal is selected from the group consisting of lanthanum, rhenium, silver, palladium, tin, molybdenum, and mixtures of two or more thereof, preferably, lanthanum.

In another aspect, the invention relates to a method of making a selectivated catalyst. In the method, a crystalline aluminosilicate comprising ZSM-5 or ZSM-11 which has hydrogen ions is provided. The crystalline aluminosilicate is contacted with a source of a first metal and/or a source of a different, second metal to form a metal-containing crystalline aluminosilicate. The first metal and the second metal are referenced above. The metal-containing crystalline aluminosilicate is selectivated by contacting it with a selectivating agent, referenced above, to form the selectivated catalyst. The selectivated catalyst may be calcined at a temperature of about 550° C. for 1 or more hours.

In other aspects, the invention relates to a process, systems, and apparatus for conversion of a feedstock comprising light paraffinic hydrocarbon to a product comprising aromatic hydrocarbon. The feedstock typically comprises one or more light hydrocarbon compounds having no more than five carbon atoms. The product typically comprises at least one single-ring aromatic hydrocarbon compound having six or more carbon atoms. Preferably, the product has a reduced amount of multi-ring aromatic compounds as compared to prior art processes. The process comprises contacting the feedstock under suitable conversion conditions in the presence of one of the selectivated catalysts of this invention, or made by one of the methods of this invention. In certain aspects, the product comprises (i) one or more single-ring aromatic hydrocarbon compounds selected from the group consisting of benzene, toluene, xylenes, and mixtures of two or more thereof; and (ii) one or more multiple-ring aromatic hydrocarbon compounds such as naphthalene.

In certain aspects, the use of the selectivated catalyst in the process typically provides at least about 40% reaction selectivity to benzene, toluene or xylenes, and mixtures thereof. Also, the use of the selectivated catalyst in the process typically provides less than about 10% reaction selectivity to multi-ring aromatic compounds, such as naphthalene.

DETAILED DESCRIPTION

The catalyst of this invention is suitably employed in a process for conversion of relatively low-value hydrocarbon, e.g., light paraffinic hydrocarbon, such as natural gas, to form aromatic hydrocarbon, e.g., single-ring aromatic hydrocarbon, such as, for example, benzene, toluene and/or xylenes. The natural gas feedstock comprises light hydrocarbon, such as, for example, light alkanes ($C_{5-}$) or light paraffin. The process includes the conversion of at least a portion of the light paraffinic hydrocarbon feedstock to produce a product comprising aromatic hydrocarbon, non-aromatic hydrocarbon, molecular hydrogen, and unconverted light paraffinic hydrocarbon feedstock.

It has been found that metal-containing zeolite-based catalysts used in a conversion process of light paraffinic hydrocarbon feedstock are selectivated by contacting with a selectivating agent. Such selectivation agents, include, but are not limited to, organo-silicates, organo-aluminates, organo-phosphates, and mixtures of two or more thereof. Such selectivation results in the process for conversion being selective to produce single-ring aromatic compounds, such as benzene, toluene and xylenes, rather than multiple-ring aromatics hydrocarbons, such as naphthalene.

Definitions

For the purpose of this specification and appended claims, the following terms are defined.

As used herein, the term "selectivated" means a method by which a zeolite, either incorporated with a binder or in unbound form, is modified when contacted at least once with a selectivating agent to deposit the selectivating agent on or proximate to the external surface of the zeolite by any suitable method.

As used herein, the term "selectivating agent" means a compound which is used to selectivate a zeolite in either bound or unbound form, such as, for example, an organo-silicate, and contains an organic group and an anionic inorganic group.

As used herein, the term "selectivity" when used in connection with a catalyst used in a process to produce a specific compound in a product stream means the moles of such specific compound produced by such catalyst per mole of the product stream. The relative selectivity of two catalysts may be compared by comparing their selectivities under substantially the same reaction conditions of temperature, pressure, composition of feedstock and weight-hourly-space-velocity (WHSV), as defined below.

As used herein, the term "$C_n$" hydrocarbon means a hydrocarbon having n carbon atom(s) per molecule, wherein n is a positive integer.

The term "$C_{n+}$" hydrocarbon means a hydrocarbon having at least n carbon atom(s) per molecule.

The term "$C_{n-}$" hydrocarbon means a hydrocarbon having no more than n carbon atom(s) per molecule.

The term "hydrocarbon" or "hydrocarbons" mean a class of compounds containing a hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, the terms "alkane", paraffin, and "paraffinic hydrocarbon" mean substantially-saturated compounds containing hydrogen and carbon only, e.g., those containing ≤1% (molar basis) of unsaturated carbon atoms. As an example, the term alkane encompasses $C_2$ to $C_{20}$ linear, iso, and cyclo-alkanes.

As used herein, the terms "unsaturated" and "unsaturated hydrocarbon" refer to one or more $C_{2+}$ hydrocarbon compounds which contain at least one carbon atom directly bound to another carbon atom by a double or triple bond.

As used herein, the terms "aromatics" and "aromatic hydrocarbon" mean a class of hydrocarbon compounds containing at least one aromatic core.

As used herein, the phrase "process for conversion" means processes which include the formation of an unsaturated cyclic compound, preferably a substituted or unsubstituted aromatic compound, such as, for example, benzene or toluene or xylene isomers, from a saturated aliphatic compound, such as, for example, ethane, propane, n-butane, or n-pentane, or from an unsaturated aliphatic compound such as, for example, ethylene, propylene or butylene.

The term "naphtha" means a mixture comprising aromatic hydrocarbon having six or more carbon atoms, also referred to as a $C_{6+}$ aromatic hydrocarbon, such as, for example, a mixed xylene.

The term "reaction zone" or "reactor zone" mean a location within a reactor, e.g., a specific volume within a reactor, for carrying out a specified reaction. A reactor or reaction stage may encompass one or more reaction zones. More than one reaction may be carried out in a reactor, reactor stage, or reaction zone.

As used herein, the term "molecular sieve of the MCM-22 family" (or "MCM-22 family material" or "MCM-22 family") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

The term "Constraint Index" is defined in U.S. Pat. Nos. 3,972,832 and 4,016,218, both of which are incorporated herein by reference.

The term "yield" refers to the production of a specified compound or a class of compounds in a catalytic reaction.

The term "conversion" when used in connection with a specified reactant in a reaction means the amount of the reactant consumed in the reaction. For example, when the specified reactant is propane ($C_3$) hydrocarbon, 100% conversion means 100% of the $C_3$ hydrocarbon is consumed in the reaction. Conversion may also be indicative of the activity of a catalyst where a higher activity catalyst has a high conversion, and a low activity catalyst has a lower activity.

The term "weight hourly space velocity", referred to as "WHSV" means the quotient of the mass flow rate of the reactants divided by the mass of the catalyst used in the reactor.

The invention includes a process for the conversion of a feedstock, such as, for example, light (e.g., $C_{5-}$ paraffinic hydrocarbon) paraffinic hydrocarbon feedstock in one or more stages to selectively convert the feedstock to form a product comprising single-ring aromatic hydrocarbon and fewer multi-ring aromatic hydrocarbon compounds. Representative feedstock will now be described in more detail. The invention is not limited to these feedstock, and this description is not meant to foreclose other feedstock within the broader scope of the invention.

Feedstock

The feedstock typically comprises one or more $C_2$ to $C_5$ hydrocarbon compounds, e.g., one or more light paraffinic hydrocarbon (i.e., $C_2$ to $C_5$) compounds. For example, the feedstock can comprise ≥1 wt. % of light hydrocarbon based on the weight of the feed, such as ≥10 wt. %, or ≥25 wt. %, or ≥50 wt. %, or ≥75 wt. %, or ≥90 wt. %, or ≥95 wt. %. Optionally, the feed further comprises diluent. Diluent present in the feed's source (e.g., methane and/or $CO_2$ present in natural gas) and diluent added to the feed are within the scope of the invention. Diluent, when present, is typically included in the feed in an amount ≤60 wt. % based on the weight of the feed, e.g., ≤50 wt. %, such as ≤40 wt. %, or ≤30 wt. %, or ≤20 wt. %, or ≤10 wt. %. A feed constituent is diluent when it is substantially non-reactive under the specified reaction conditions in the presence of the specified catalyst, e.g., methane, molecular nitrogen, and inert atomic gasses such as argon.

The feedstock typically contains $C_3$ and/or $C_4$ hydrocarbon e.g., (i) ≥20 wt. % propane, such as ≥40 wt. %, or ≥60 wt. %, and/or (ii) ≥20 wt. % butanes, such as ≥40 wt. %, or ≥60 wt. %. Although the feedstock may contain $C_5$ hydrocarbon, the amount of $C_5$ hydrocarbon when present is typically small, e.g., ≤20 wt. %, such as ≤10 wt. %, or ≤1 wt. %. Typically, the feedstock contains ≤10 wt. % of $C_{6+}$ saturated hydrocarbon, e.g., ≤5 wt. %, or ≤1 wt. %.

The feedstock may also contain methane (a $C_1$ hydrocarbon), e.g., ≥1 wt. % methane, such as ≥10 wt. %, or ≥20 wt. %, or ≥30 wt. %. Even though methane is a diluent, i.e., it does not typically react to produce single-ring or multiple-ring aromatic hydrocarbon in the presence of the specified selectivated catalyst under the specified reaction conditions, its presence may be beneficial for decreasing the partial pressure of $C_2$ to $C_5$ hydrocarbon.

Optionally, the feedstock contains unsaturated $C_{2+}$ hydrocarbon, such as one or more $C_2$-$C_5$ unsaturated hydrocarbon compounds. When present, the amount of $C_{2+}$ unsaturated hydrocarbon is typically ≤20 wt. %, e.g., ≤10 wt. %, such as ≤1 wt. %, or ≤0.1 wt. %, or in the range of from 0.1 wt. % to 10 wt. %. More particularly, the feedstock is generally one that is substantially-free of aromatic hydrocarbon, where substantially-free in this context means an aromatic hydrocarbon content that is ≤1 wt. % based on the weight of the feedstock, such as ≤0.1 wt. %, or ≤0.01 wt. %, or ≤0.001 wt. %.

The feedstock may be obtained from one or more sources of hydrocarbon, e.g., from natural hydrocarbon sources such as those associated with producing petroleum, or from one or more synthetic hydrocarbon sources such as catalytic and non-catalytic reactions. Examples of such reactions include, catalytic cracking, catalytic reforming, coking, steam cracking, etc. Synthetic hydrocarbon sources include those in which hydrocarbon within a geological formation has been purposefully subjected to one or more chemical transformations. The feed can include recycle components, e.g., portions of the first and/or second product, such as portions of the first and/or second raffinate. Such recycle, when used, can include, e.g., methane, molecular hydrogen, and $C_{2+}$ hydrocarbon, typically $C_2$ to $C_5$ hydrocarbon.

In certain aspects, the source of the feedstock includes natural gas, e.g., raw natural gas ("raw gas"). Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more of petroleum deposits, coal deposits, and shale deposits. The natural gas can be one that is obtained by conventional productions methods but the invention is not limited thereto. Raw natural gas is a natural gas obtained from a geologic formation without intervening processing, except for (i) treatments to remove impurities such as water and/or any other liquids, mercaptans, hydrogen sulfide, carbon dioxide; and (ii) vapor-liquid separation, e.g., for adjusting the relative amounts of hydrocarbon compounds (particularly the relative amounts of $C_{4+}$ hydrocarbon compounds) in the natural gas; but not including (iii) fractionation with reflux. Conventional methods can be used for removing impurities and/or adjusting the relative amount of hydrocarbon compounds present in the feed, but the invention is not limited thereto. For example, certain components in the natural gas can be liquefied by exposing the natural gas to a temperature in the range of −57° C. to 15° C., e.g., −46° C. to 5° C., such as −35° C. to −5° C. At least a portion of the liquid phase can be separated in one or more vapor-liquid separators, e.g., one or more flash drums. One suitable raw natural gas comprises 3 mole % to 70 mole % methane, 10 mole % to 50 mole % ethane, 10 mole % to 40 mole % propane, and 5 mole % to 40 mole % butanes and 1 mole % to 10 mole % of total $C_5$ to $C_9$ hydrocarbon. In certain aspects, ≥50 wt. % of the feed comprises natural gas, such as raw natural gas, e.g., ≥75 wt. %, or ≥90 wt. %, or ≥95 wt. %.

Any form of raw gas can be used as a source material, although the raw gas is typically one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |
| $CH_4$ | 0-80 (64.48) | 0-97 (91.01) | 0-98 (94.87) |
| $C_2H_6$ | 5-20 (11.98) | 2-10 (4.88) | 1-5 (2.89) |
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.01-1 (0.09) |

In certain aspects, the feed comprises ≥75 wt. % Associated Gas, based on the weight of the feed, e.g., ≥90 wt. %, or ≥95 wt. %. Associated Gas is typically found with petroleum deposits, e.g., dissolved in the oil or as a free "gas cap" above the oil in a reservoir. In conventional petroleum production, the lack of effective natural transportation facilities, e.g., the lack of natural gas liquefaction and/or pipeline facilities, typically results in Associated Gas being stranded at or near the reservoir. This in turn can lead to undesirable natural gas flaring. Moreover, even in locations where pipeline facilities are available, Associated Gas may be excluded from the pipeline because it typically exceeds one or more of the following typical pipeline specifications: ≤12 wt. % ethane, ≤5 wt. % propane, ≤2 wt. % butanes, a Wobbe Index of from 49.01 MJ/sm$^3$ to 52.22 MJ/sm$^3$, and a heating value of from 36.07 MJ/sm$^3$ to 41.40 MJ/sm$^3$.

Since methane is not detrimental to the process, and is in at least some aspects beneficial, the invention obviates the need for costly and inefficient cryogenic methane separation facilities, such as one or more conventional cold boxes. Typically, obtaining the feed from the source material (e.g., natural gas, such as raw gas) does not include (i) exposing the feed, source material, or any intermediate thereof to a temperature ≤−37° C., e.g., ≤−46° C., such as ≤−60° C. Certain aspects of the invention do not include cryogenic processing, e.g., cryogenic methane separation is not used.

The invention therefore particularly advantageous in remote or under-developed locations, where (i) the lack of cryogenic methane separation facilities limits the utility of conventional natural gas aromatization processes, (ii) the lack of a pipeline or natural gas production infrastructure, may result in significant quantities of light hydrocarbon being flared or burned as fuel, and (iii) Associated Gas remains stranded at a remote location for lack of pipeline facilities or a failure to meet one or more specifications of an available pipeline. Small scale plants using the present process would allow effective recovery of these light hydrocarbon resources as liquid hydrocarbons.

The feedstock is conducted to one or more reaction stages, where it is reacted in the presence of at least one catalyst for conversion in at least one reaction zone operating under suitable conversion conditions. The reaction converts at least a portion of the feedstock's light hydrocarbon to a product comprising desirable single-ring aromatic hydrocarbon. Since the catalyst is a selectivated catalyst, the process produces fewer undesirable multiple-ring aromatic hydrocarbon compounds than do conventional processes utilizing substantially the same feed and substantically the same process conditions. Certain aspects of the selectivated catalyst, its method of making and use in conversion processes will now be described in more detail. The invention is not limited to these aspects, and this description is not meant to foreclose other aspects within the broader scope of the invention.

Catalysts

The catalysts can include selectivated catalysts which comprise a crystalline aluminosilicate zeolite having a Constraint Index of less than 12, preferably, in the range of about 1 to about 12, a first metal and at least one selectivating agent. Optionally, the selectivated catalysts further comprises a second metal in addition to the first metal. The second metal is different from the first metal. The selectivated catalyst contains at least about 0.005 wt. % of the first metal, or from about 0.005 wt. % to about 1.0 wt. % of said first metal, or from about 0.01 wt. % to about 1.5 wt. % of said first metal, based on the weight of said selectivated catalyst. The selectivated catalyst typically contains at least about 0.005 wt. % of the second metal, or from about 0.005 wt. % to about 1.0 wt. % of said second metal, or from about 0.01 wt. % to about 1.5 wt. % of said second metal, based on the weight of said selectivated catalyst.

Typically, the crystalline aluminosilicate zeolite has a medium pore size and a Constraint Index of less than or equal to about 12. Examples of suitable zeolites include ZSM-5, ZSM-11, ZSM-12, ZSM-21, ZSM-22, ZSM-23, ZSM-35, ZSM-38, ZSM-48 ZSM-50, ZSM-57, and MCM-68, including mixtures and intermediates thereof such as ZSM-5/ZSM-11 admixture. ZSM-5 is described in U.S. Pat. No. 3,702,886 and Re. 29,948. ZSM-11 is described in U.S. Pat. No. 3,709,979. A ZSM-5/ZSM-11 intermediate structure is described in U.S. Pat. No. 4,229,424. ZSM-12 is described in U.S. Pat. No. 3,832,449. Zeolite ZSM-21 is described U.S. Pat. No. 4,082,805. ZSM-22 is described in U.S. Pat. No. 4,556,477. ZSM-23 is described in U.S. Pat. No. 4,076,842. ZSM-35 is described in U.S. Pat. No. 4,016,245. ZSM-38 is described in U.S. Pat. No. 4,046,859. ZSM-48 is described in U.S. Pat. No. 4,234,231. ZSM-50 is described in U.S. Pat. No. 4,640,826. ZSM-57 is described in U.S. Pat. No. 4,873,067. TEA-Mordenite is described in U.S. Pat. Nos. 3,766,093 and 3,894,104. MCM-68 is described in U.S. Pat. No. 6,049,018.

The aluminosilicate zeolite's silica-to-alumina ($Si:Al_2$) atomic ratio is typically ≥2 molar, e.g., in the range of 10 to 300 molar, or in the range of from 5 to 100 molar. The silica-to-alumina ratio, $Si:Al_2$, is meant to represent the $Si:Al_2$ atomic ratio in the rigid anionic framework of the crystalline aluminosilicate zeolite. In other words, aluminum in (i) any matrix or binder or (ii) in cationic or other form within the crystalline aluminosilicate zeolite's channels is excluded from the $Si:Al_2$ atomic ratio. Zeolites having a higher silica-to-alumina ratio can be utilized when a lower catalyst acidity is desired, e.g., in the range of from 44 to 100 molar, such as from 50 to 80 molar, or 55 to 75 molar.

The crystalline aluminosilicate zeolite can have a Constraint Index in the range of about 1 to 12 and is selected from the group consisting of a MCM-22 family material, ZSM-5, ZSM-11, ZSM-12, ZSM-21, ZSM-22, ZSM-23, ZSM-35, ZSM-38, ZSM-48, ZSM-50, ZSM-57, MCM-68 and mixtures of two or more thereof. Preferably, the aluminosilicate zeolite is ZSM-11 or H-ZSM-11 (the acidic form of ZSM-11), and more preferably, the aluminosilicate zeolite is ZSM-5 or H-ZSM-5 (the acidic form of ZSM-5).

In certain aspects, the molecular sieve has a relatively small crystal size, e.g., small crystal ZSM-5, meaning ZSM-5 having a crystal size ≤0.05 μm, such as in the range of 0.02 μm to 0.05 μm. Small crystal ZSM-5 and the method for determining molecular sieve crystal size are disclosed in U.S. Pat. No. 6,670,517, which is incorporated by reference herein in its entirety.

In other aspects, the crystalline aluminosilicate zeolite comprises at least one molecular sieve of the MCM-22 family, e.g., MCM-22 alone or in combination with other aluminosilicates, specified above, or other MCM-22 family materials. Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), and ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve component.

In one or more embodiments, the crystalline aluminosilicate is in the hydrogen form and has hydrogen ions, e.g., the crystalline aluminosilicate is in acidic form.

The catalyst comprises a molecular sieve, a first metal and optionally a second metal, and at least one selectivating agent. The molecular sieve is preferably an aluminosilicate zeolite, in an amount of ≥20 wt. %, based on the weight of the catalyst, e.g., ≥25 wt. %, such as in the range of from 30 wt. % to 99.9 wt. %. In one or more embodiments, the molecular sieve comprises at least one aluminosilicate zeolite in an amount of ≥90 wt. %. The molecular sieve component may consist essentially of or even consist of an aluminosilicate zeolite. The zeolite may be one that is in hydrogen form, e.g., one that has been synthesized in the alkali metal form, but is then converted from the alkali to the hydrogen form and has hydrogen ions, e.g., acidic.

The first metal can be one or more neutral metals selected from Groups 3-14 of the Periodic Table, such as one or more of Ga, In, Zn, Cu, W, Fe, and Pt; and/or one or more oxides, sulfides and/or carbides of these metals. The first metal is typically selected from the group consisting of zinc, gallium, platinum, copper, rhenium, iron, and mixtures of two or more first metals thereof. Preferably the first metal is zinc and/or gallium, e.g., zinc.

The second metal is also a neutral metal, oxide, sulfide, and/or carbide of metal selected from Groups 3-14 of the Periodic Table, but the first metal is not the same as the first metal. The second metal is typically selected from the group consisting of lanthanum, rhenium, silver, palladium, tin, molybdenum, and mixtures of two or more thereof. Preferably, the second metal is lanthanum, i.e., La.

The catalyst comprises from at least about 0.005 wt. %, or 0.01 wt. %, or 0.05 wt. %, or 0.10 wt. % up to about 1.0 wt. %, 2.0 wt. %, 3.0 wt. %, or 4.0 wt. %, or 5.0 wt. %, or 10.0 wt. % of the first metal and the second metal, based on the weight of the catalyst. The catalyst may comprise from about 0.2 wt. % of the first metal and the second metal, such as ≥0.5 wt. % up to 1.0 wt. %, 2.0 wt. %, 3.0 wt. %, or 4.0 wt. %, or 5.0 wt. % of such first metal and the second metal. The first metal and the second metal, based on the weight of the catalyst, is in the preferred range from at least about 0.01 wt. % up to about 1.5 wt. %, more preferably, in the range of at least about 0.005 wt. % up to about 1.5 wt. %, or most preferably, in the range of at least about 0.005 wt. % up to about 1.0 wt. %.

In addition to the molecular sieve, and the first metal and optionally the second metal, the catalyst of this invention is modified by the addition of a selectivating agent. The selectivating agent is selected from the group consisting of an organo-silicate, an organo-aluminate, an organo-phosphate, and mixtures of two or more thereof. For example, the organo-silicate selectivating agent can be a tetraalkyl orthosilicate selected from the group consisting of a tetramethyl orthosilicate (TMOS), a tetraethyl orthosilicate (TEOS), a tetrapropyl orthosilicate (TPOS), and mixtures of two or more thereof. Preferably, the selectivating agent is tetraethyl orthosilicate (TEOS).

The amount of the selectivating agent added is typically at least about 0.005 wt. %, or 0.01 wt. %, or 0.05 wt. %, or 0.10 wt. %, 0.2 wt. % up to about 1.0 wt. %, 2.0 wt. %, 3.0 wt. %, or 4.0 wt. %, or 5.0 wt. %, or 10.0 wt. % of selectivating agent, based on the weight of the catalyst. Preferably the amount of selectivating agent is 1.0 wt. %, based on the weight of the catalyst. The selectivating agent can be deposited on, into, and/or proximate to the catalyst after the first metal or the optional second metal has been deposited on, into, and/or proximate to the catalyst. Typically, the selectivating agent is deposited upon the first metal, preferably, zinc, and/or upon the optional second metal (when the second metal is present), preferably, lanthanum.

Alternatively, or in addition, the selectivating agent can be deposited before the first metal or the optional second metal has been deposited. Put another way, the selectivating agent can be deposited first, the first metal, preferably, zinc, and/or optional second metal, preferably, lanthanum is then deposited on the selectivated catalyst.

Not to be bound by theory, it is believed that the deposition of selectivating agent on, in, or proximate to the crystalline aluminosilicate to form the selectivated catalyst helps to modify the size of its pores and thus limiting the size of the reactants and products which can enter and exit the modified pores. It is believed that when the crystalline aluminosilicate, such as for example, ZSM-5, is treated with a source of the first metal, preferably zinc, and the optional second metal, preferably lanthanum, the metal(s) associates itself with the acid sites on the crystalline aluminosilicate's pores and/or external surfaces, thereby increasing its activity. Thereafter, when the metal(s)-containing crystalline molecular sieve component is treated with the selectivating agent the pores are structured to facilitate the formation of single-ring aromatic hydrocarbon, such as benzene, toluene and xylenes, and reduced formation of multiple-ring aromatic hydrocarbon, such as naphthalene.

The catalyst of this invention provides an increased reaction selectivity towards the desirable single-ring aromatic hydrocarbon. In one or more embodiments, the catalyst provides a reaction selectivity to such single-ring aromatic hydrocarbons of over 35 wt. %, or over 40 wt. %, or preferably over 45 wt. %, under suitable conversion conditions, preferably conditions which include at least a temperature in the range of about 400° C. to 750° C., e.g., 450° C. to about 750° C., or from about 450° C. to 650° C.; a pressure of from about 35 kPa to about 1480 kPa, and a WHSV from 0.1 to 20 hr$^{-1}$.

The catalyst has a reduced reaction selectivity to the undesireable multiple-ring aromatic hydrocarbons. In certain aspects, the catalyst provides a reaction selectivity to such multiple-ring aromatic hydrocarbons of less than 5 wt. %, less than 10 wt. %, preferably less than 15 wt. %, under suitable conversion conditions, preferably conditions which include at least a temperature in the range of about 450° C. to about 650° C., a pressure of from about 35 kPa to about 1480 kPa, and a WHSV from 0.1 to 20 hr$^{-1}$.

In certain aspects that are particularly suitable for dehydrocyclization, the catalyst is a selectivated catalyst which comprises (a) ZSM-5 or ZSM-11; (b) 0.005 wt. % to about 1.5 wt. % of zinc and optionally 0.005 wt. % to about 1.5 wt. % of lanthanum, each based on the weight of said selectivated catalyst; and (c) at least 0.005 wt. % of a tetraalkyl orthosilicate selectivating agent, based on the weight of said selectivated catalyst, said tetraalkyl orthosilicate selectivating agent is selected from the group consisting of a tetramethyl orthosilicate (TMOS), a tetraethyl orthosilicate (TEOS), a tetrapropyl orthosilicate (TPOS), and mixtures of two or more thereof, wherein said selectivated catalyst provides over about 40% reaction selectivity to benzene, toluene or xylenes single-ring aromatic hydrocarbons, and mixtures thereof, and/or less than about 10% reaction selectivity to naphthalene multiple-ring aromatics, in the conversion of a light paraffinic hydrocarbon feedstock comprising one or more light hydrocarbons having no more than five carbon atoms to form a product comprising at least one single-ring aromatic hydrocarbon under conversion conditions which include at least a temperature in the range of about 450° C. to about 750° C., a pressure in the range of from about 35 kPa to about 1480 kPa, and a WHSV from about 0.1 to about 20 hr$^{-1}$.

In one or more embodiments, the catalyst of this invention for the conversion of a light paraffinic hydrocarbon feedstock comprising light $C_{5-}$ hydrocarbon to form single-ring aromatic hydrocarbon is made by any one of the methods disclosed hereinafter.

Method of Making the Catalyst

Certain aspects relate to methods of making one or more of the specified catalysts for use in the process for the conversion of a light paraffinic hydrocarbon feedstock. The method includes providing a crystalline aluminosilicate having a Constraint Index of less than or equal to about 12, preferably in the range of about 1 to about 12, more preferably, a crystalline aluminosilicate comprising ZSM-5 or ZSM-11. In a contacting step, the crystalline aluminosilicate is contacted with a source of a first metal and optionally a source of a second metal under conditions sufficient to deposit said first metal and said optional second metal on, in, or proximate to the crystalline aluminosilicate, and to form a metal-containing crystalline aluminosilicate. If both metals are used, the first metal is different from the second metal. The first metal is typically selected from Groups 3-14 of the Periodic Table, and can be in the form of one or more of neutral metal, metal oxide, metal sulfide, and metal carbide. For example, the metal can be selected from the group consisting of zinc, gallium, platinum, copper, rhenium, iron, and mixtures of two or more thereof. The second metal is also selected from Groups 3-14 of the Periodic Table. For example, the second metal can be selected from the group consisting of lanthanum, rhenium, silver, palladium, tin, molybdenum, and mixtures of two or more thereof. In a selectivating step, the metal-containing crystalline aluminosilicate is selectivated by contacting with a selectivating agent under conditions sufficient to deposit said selectivating agent on said metal-containing crystalline aluminosilicate to form said selectivated catalyst. In one or more embodiments, the selectivating step is performed before the contacting step.

The first metal and the optional second metal may be deposited on, in, or proximate to the crystalline aluminosilicate by conventional methods, such as, for example, by impregnation or ion exchange of the molecular sieve with a solution of a compound of the relevant metal. Non-limiting examples of the conditions effective to deposit the metals on the crystalline aluminosilicate or the selectivated aluminosilicate are set forth in the Examples.

The selectivating agent may be deposited on the metal-containing aluminosilicate, or crystalline aluminosilicate alone, by any suitable method, e.g., by impregnating the selectivating agent onto the external surface of the crystalline aluminosilicate. A selectivating agent may be dissolved in an organic carrier, mixed with the catalyst, and then dried by evaporation or vacuum distillation. This method is termed "impregnation". Other conventional methods may be utilized to do so, and the invention is not limited to any one specific method. Non-limiting examples of the conditions effective to deposit the selectivating agent on the metal-containing aluminosilicate, or crystalline aluminosilicate alone, are set forth in the Examples.

The selectivating agent can be a tetraalkyl orthosilicate selected from the group consisting of a tetramethyl orthosilicate (TMOS), a tetraethyl orthosilicate (TEOS), a tetrapropyl orthosilicate (TPOS), and mixtures of two or more thereof. Preferably, the selectivating agent is tetraethylorthosilicate.

The catalyst may be calcined in air after treatment with the selectivating agent. In one or more embodiments, the method of making the selectivated catalyst further comprises a calcining step in which the selectivated catalyst is calcined by heating at a temperature of about 550° C. for 1 or more hours. One non-limiting suitable calcination procedure after treatment with TEOS is set forth in the Examples.

When the first metal is zinc, non-limiting suitable sources of zinc are selected from the group consisting of zinc nitrate, zinc titanate, zinc silicate, zinc borate, zinc fluorosilicate, zinc fluorotitanate, zinc molybdate, zinc chromate, zinc tungstate, zinc zirconate, zinc chromite, zinc aluminate, zinc phosphate, zinc acetate dihydrate, diethyl zinc, zinc 2-ethylhexanoate, and mixtures of two or more thereof.

When the second metal is lanthanum, non-limiting suitable sources of lanthanum include a lanthanum salt, a lanthanum nitrate, or a mixture thereof.

The catalyst can include the crystalline aluminosilicate in unbound form, that is, without a binder or matrix material. In particular, the catalyst can be substantially free of binder, e.g., contains ≤1 wt. % of binder, such as ≤0.1 wt. %. For example, the catalyst's crystalline aluminosilicate can comprises ≥95 wt. % of molecular sieve, e.g., ≥95 wt. % of ZSM-5, and in particular small crystal H-ZSM-5.

The crystalline aluminosilicate or the catalyst, before or after selectivation, may be combined in a conventional manner with an optional matrix component, e.g., one or more inorganic binders. A matrix component may be used, e.g., to make the catalyst more resistant to the temperatures and other conditions employed in the process for conversion. The amount of matrix component is not critical. When present, the amount of matrix component is typically in the range of 0.01 to about 0.9 times the weight of the catalyst, preferably, the selectivated catalyst, e.g., in the range of 0.02 to 0.8. The matrix component may include active materials, such as synthetic or naturally occurring zeolites.

Alternatively, or in addition, the matrix component may include clays and/or oxides such as alumina, silica, silica-alumina, zirconia, titania, magnesia or mixtures of these and other oxides. The matrix component may include naturally occurring materials and/or materials in the form of gelatinous precipitates or gels including mixtures of silica and metal oxides. Clays may also be included with the oxide type binders to modify the mechanical properties of the catalyst or to assist in its manufacture. Alternatively or in addition, the matrix component may include one or more substantially inactive materials. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve thermal and strength properties (e.g., crush strength) of the catalyst under catalytic conversion conditions.

Process

In still another aspect, the invention is a process for the conversion in one or more reaction zones of a light paraffinic hydrocarbon feedstock comprising one or more light hydrocarbons having no more than five carbon atoms to form a product comprising at least one single-ring aromatic hydrocarbon having six or more carbon atoms. The process comprises the steps of contacting said feedstock under suitable conversion conditions in the presence of any one of the catalysts, preferably, selectivated catalysts, of this invention to form said product.

In one or more embodiments, the catalyst of this invention when used in the process provides an increased reaction selectivity towards the desirable single-ring aromatic hydrocarbon. That is, more of the desirable single-ring aromatic hydrocarbon, such as benzene, toluene and xylenes, is made. The reaction selectivity to such single-ring aromatic hydrocarbons is over 35 wt. %, or over 40 wt. %, or preferably over 45 wt. %, under suitable conversion conditions, preferably conditions which include at least a temperature of about 450° C. to about 750° C., or from about 450° C. to 650° C., a pressure of from about 35 kPa to about 1480 kPa and a WHSV from 0.1 to 20 hr$^{-1}$.

In one or more embodiments, the catalyst of this invention when used in the process forms a reduced reaction selectivity to the undesireable multiple-ring aromatic hydrocarbons. That is, less of the undesirable multiple-ring aromatic hydrocarbon, such as naphthalene, is made. In one or more embodiments, the catalyst provides a reaction selectivity to such multiple-ring aromatic hydrocarbons of preferably less than 5 wt. %, or less than 10 wt. %, or less than 15 wt. %, under suitable conversion conditions. Preferably, such suitable conversion conditions include at least a temperature in the range of about 450° C. to about 650° C., a pressure of from about 35 kPa to about 1480 kPa and a WHSV from 0.1 to 20 hr$^{-1}$.

One or more of the light hydrocarbon (e.g., of the light paraffinic hydrocarbon feedstock) has no more than five carbon atoms. The light hydrocarbon is selected from the group consisting of methane, ethane, propane, butane and mixtures of two or more thereof. Preferably, the light hydrocarbon is ethane or propane.

The single-ring aromatic hydrocarbon which has six or more carbon atoms of the product is selected from the group consisting of benzene, toluene, xylenes and mixtures of two or more thereof. Preferably, the single-ring aromatic hydrocarbon is benzene or toluene.

Suitable conversion conditions include at least a temperature in the range of about 450° C. to about 750° C., or from 450° C. to 650° C., a pressure in the range of from about 35 kPa to about 1480 kPa and a WHSV from 0.1 to 20 hr$^{-1}$. In other embodiments, such conditions include a temperature in the range of from 400° C. to 630° C., and a pressure in the range of from about 138 kPa (20 psia) to about 2070 kPa (300 psia). Typically, the temperature is in the range of from 450° C. to 605° C., the pressure is in the range of from about 207 kPa (30 psia) to about 522 kPa (80 psia), and suitable conversion conditions include a weight hourly space velocity (WHSV) in the range of from 0.1 to 10 hr$^{-1}$.

One or more reaction zones have one or more stages containing at least one bed of the specified catalyst. The catalyst may be in particulate form, as the conversion reaction takes place as the feedstock traverses the catalyst bed. The catalyst bed may be one or more of a fixed, moving, or fluidized catalyst bed.

In one or more embodiments, the process further comprises a fixed catalyst bed reaction zone for contacting said feedstock under said suitable conversion conditions in the presence of said catalyst of this invention. The fixed catalyst bed is disposed in the reaction zone. In a fixed catalyst bed (also called a packed bed), the catalyst remains stationary in the reaction zone. In downflow mode, the feedstock enters the first reaction zone proximate to the upstream end of a reactor. After the conversion reaction is carried out in the bed, the product exits the first reaction zone near the downstream end of the reactor. In upflow mode, the flow is in the reverse direction. The reaction zone within the reactor establishes a fixed reference frame, and the catalyst bed is "fixed" in the sense that it is substantially immobile with respect to the fixed reference frame during the conversion reaction. The reactor may be, e.g., an adiabatic single bed, a multi-tube surrounded with heat exchange fluid or an adiabatic multi-bed with internal heat exchange, among others. At least one substantially similar second reaction zone may be operated in parallel with the first reaction zone, so that first reaction zone may be operated in reaction mode while the second reaction zone is operated in regeneration mode, to regenerate the second reaction zone's catalyst. Continuous or semi-continuous operation may be carried out by alternating reaction and regeneration modes in the first and second reaction zones.

In one or more embodiments, the process further comprises a moving catalyst bed or a fluidized catalyst bed reaction zone for contacting said feedstock under said suitable conversion conditions in the presence of said catalyst. The moving or fluidized catalyst bed is disposed in the reactor zone. In a moving catalyst bed, particles of the specified catalyst flow under the influence of an external force such as gravity. The catalyst particles substantially maintain their relative positions to one another during the flow, resulting in a movement of the bed with respect to the fixed reference frame. Average flow of the specified feedstock with respect to the catalyst flow may be concurrent, countercurrent, or cross-current.

In a fluidized bed, a fluidizing medium (typically in the vapor phase) is conducted through the catalyst bed at a velocity sufficient to suspend the catalyst particles within the bed. The bed suspended catalyst particles typically has the appearance of a boiling fluid. The fluidizing medium's velocity is selected such that the fluidizing medium exerts a sufficient force on the catalyst particles to substantially balance the weight of the catalyst bed.

Conventional fixed, moving, and/or fluidized beds may be used in the first reaction zone, and optionally in the second reaction zone, but the invention is not limited thereto.
Representative Reactors The term "reaction zone" or "reactor zone" mean a location within a reactor, e.g., a specific volume within a reactor, for carrying out a specified reaction. A reactor or reaction stage can encompass one or more reaction zones. More than one reaction can be carried out in a reactor, reactor stage, or reaction zone. For example, a reaction stage can include a first zone for carrying out first and second reactions and a second zone for carrying out a third reaction, where the first reaction (e.g., dehydrocyclization using one or more of the specified catalysts) can be the same as or different from the second reaction, and the third reaction (e.g., $CO_2$ methanation) can be the same as or different from the second reaction. A reaction can feature an average residence time of the catalyst in the reaction zone under the reaction conditions. The catalyst can, e.g., reside in a fixed catalyst bed located in a zone of a reactor. In these configurations, the zone is a reaction zone when the catalyst is exposed to the desired feed under the desired reaction conditions (reaction mode). The zone is a regeneration zone when the catalyst is exposed to a regeneration medium (e.g., air) under catalyst regeneration conditions (regeneration mode). These configurations can be operated continuously by switching between reaction mode and regeneration mode cyclically (e.g., in sequence). In these configurations, the average residence time is the average time the catalyst in the zone is exposed to the desired feed and the desired reaction conditions, e.g., the average time between the start of reaction mode operation and the start of regeneration mode operation, such as the average duration of reaction mode operation. For typical catalyst beds, the average residence time is the time period from (i) the time at which a bed of fresh or freshly regenerated catalyst is first exposed to the specified catalytic dehydrocyclization conditions to (ii) the time at which the catalyst bed is removed from dehydrocyclization service, e.g., for replacement and/or regeneration. A fixed catalyst bed can be removed from dehydrocyclization service by, e.g., discontinuing feed flow and/or exposing the bed to conditions other than the specified dehydrocyclization conditions. In cyclic operation over repeated reaction and regeneration modes, the time period is numerically averaged over the number of cycles. In other configurations, a reaction zone and regeneration zone operate at the same time, e.g., in separate vessels. For example, a first bed of catalyst particles can be located in the reaction zone, with a second bed of catalyst particles located in the regeneration zone. Catalyst particles withdrawn from the reaction zone bed can be transferred to the regeneration zone's bed for regeneration. In typical fluidized bed operation, the catalyst is removed from dehydrocyclization service by gradually withdrawing catalyst particles from the bed (e.g., at a substantially constant rate) until 100% of the bed's mass is removed. In these aspects, the average time period is the average amount of time needed to remove 100% of the bed's catalyst particles.

It has been discovered that a feed conversion greater than 65 wt. % can be achieved, even with relatively refractory feeds such as ethane, when the average residence time of the catalyst in the reaction zone under reaction conditions is about 90 seconds or less. It has also been found that decreasing the catalyst's average residence time in the reaction zone under the reaction conditions to duration of 90 seconds or less increases conversion of the feed's non-aromatic hydrocarbon without significantly increasing methane selectivity. This feature is particularly useful for natural gas dehydrocyclization, and especially so when the dehydrocyclization is carried out at a relatively large space velocity.

Typically, the dehydrocyclization catalyst has an average residence time in the reaction zone under the dehydrocyclization conditions of ≤60 seconds, e.g., ≤30 seconds, such as ≤10 seconds, or ≤1 second, or ≤0.1 second. For example, the catalyst can have an average residence time in the reaction zone under the dehydrocyclization conditions in the range of from 0.001 seconds to 10 seconds, e.g., 0.01 seconds to 10 seconds, such as 0.1 seconds to 10 seconds.

In certain aspects, the catalyst is utilized for the dehydrocyclization of a feed which comprises ethane, optionally at an average residence time in the reaction zone under the dehydrocyclization conditions of ≤90 seconds. These aspects will now be described in more detail. The invention is not limited to these aspects, and this description is not meant to foreclose other aspects within the broader scope of the invention.
Representative Ethane Conversion Conditions In other aspects, e.g., those where it is desired to convert ≥50 wt. % of the feed's ethane, the process conditions can include a temperature in the range of from 450° C. to 700° C., and a pressure ≤35 psia (241.3 kPa). Typically, the conditions include a temperature in the range of from 500° C. to 675° C. and a pressure ≤34 psia (234.4 kPa), e.g., ≤32 psia (220.6 kPa), such as ≤30 psia (207 kPa), or in the range of from 10 psia (68.9 kPa) to 35 psia (241.3 kPa) or from 12 psia (82.8 kPa) to 34 psia (234.4 kPa). The indicated temperature represents an average temperature across the catalyst bed, and the indicated pressure corresponds to the pressure at the inlet of the catalyst bed. Typically, the average temperature across a bed of the catalyst is ≤700° C. Typically, the feed is not exposed to a temperature ≥700° C. at the inlet to the catalyst bed. The process can be operated in catalyst beds arranged in series, e.g., with a $C_{2+}$ non-aromatic hydrocarbon feed first contacting a bed of a first active material corresponding to one or more of the specified catalysts, with the effluent from the first catalyst bed contacting a second bed containing a second active material which is independently selected from among one or more of the specified catalysts. The second active material can be the same as or different from the first active material. The first bed may be operated under conditions (e.g., T and P) which convert primarily $C_{3+}$ non-aromatic hydrocarbon. The second bed may be operated under conditions (e.g., T and P) favorable for ethane conversion. Although they are not required, these aspects are compatible with additional processing, e.g., one or more of heating the first bed's effluent upstream of the second bed, removing at least a portion of any aromatic hydrocarbon in the first bed's effluent upstream of the second bed, removing at least a portion of any molecular hydrogen in the first bed's effluent upstream of the second bed.
Catalyst Regeneration In certain aspects, a dehydrocyclization reaction is carried out in a plurality of reactors, each reactor containing at least one bed of an active material selected from among the specified catalysts. Each of the reactors can be substantially the same as the others, namely of substantially the same bed configuration and contain substantially the same amount of substantially the same catalyst. Typically, one or more of the reactors in reaction (dehydrocyclization) mode while the other(s) are operated in regeneration mode, and vice versa. Continuous or semi-continuous operation can be carried out in each stage, e.g., by alternating reactors in sequence in reaction and regeneration modes.

Catalyst regeneration includes removing at least a portion of any accumulated deposits from the catalyst, e.g., coke and/or coke precursors. Typically, the catalyst is regenerated at an inlet temperature ≤700° C. Exceeding this temperature during regeneration has been found to result in catalyst de-alumination and/or loss of structure, leading to an undesirable loss of catalyst acidity. Catalyst regeneration for any of the specified catalysts is typically carried out using procedures which limit the maximum temperature to which the catalyst is exposed during regeneration to about 750° C., more typically to about 650° C. Conventional catalyst regeneration methods can be used, e.g., exposing the catalyst to at least one regeneration medium, e.g., an oxidant such as air or oxygen in air, for a time sufficient to remove at least a portion of the catalyst coke, but the invention is not limited thereto. Relatively uncommon regeneration media are within the scope of the invention, e.g., carbon dioxide, and/or molecular hydrogen. Typically, regeneration includes circulating a stream of regeneration media containing a limited amount of oxygen, which limits the size of the exotherm where coke is burned off the catalyst. At the location where the regeneration media (typically gaseous) enters the first (most upstream, with respect to the flow of regeneration gas) reactor, e.g., at the reactor's inlet, the regeneration media is typically exposed to a temperature ≤350° C., e.g., ≤325° C. such as ≤300° C. If needed, the oxidant content of the regeneration media can be decreased to lessen the risk of exceeding the maximum temperature. Alternatively, or in addition, regeneration can be carried out by passing a regeneration media comprising a stream of molecular hydrogen in proximity to the catalyst, e.g., for catalyst coke methanation.

Representative Fluidized Bed Conditions

Although fixed catalyst beds, moving catalyst beds, fluidized catalyst beds, ebullating catalyst beds, combinations thereof, etc., are all within the scope of the invention, certain aspects which include carrying out dehydrocyclization in one or more fluidized beds will now be described in more detail. The invention is not limited to these aspects, and this description is not meant to foreclose the use of other catalyst bed configurations within the broader scope of the invention.

In fluidized bed aspects, the dehydrocyclization catalyst is typically in the form of a plurality of catalyst particles. The catalyst particles have an average catalyst particle residence time in the reaction zone of ≤90 seconds. The dehydrocyclization reaction is typically carried out in a reaction zone, typically located in a first vessel. Catalyst regeneration is carried out in a regeneration zone, typically located in a second vessel. During typical fluid bed operation, a portion of the dehydrocyclization catalyst is continuously transferred from the reaction zone to the regeneration zone, and regenerated dehydrocyclization catalyst is continuously transferred from the regeneration zone to the reaction zone. Besides being a convenient configuration for maintaining the specified average catalyst particle residence time in the reaction zone, using a fluidized catalyst bed can be operated at a lesser pressure drop than fixed bed configurations of approximately the same capacity. Improved temperature control within the dehydrocyclization reaction zone is also typically achieved over fixed bed configurations, which desirably allows the bed to be more isothermal. Any convenient form of fluidized bed reactor can be used for carrying out the dehydrocyclization reaction, including conventional fluid bed reactors such as those described (for a different purpose) in U.S. Pat. No. 4,751,338.

During typical fluid bed operation, the feed is passed for injection into a reactor vessel through one or more injectors proximate to a distributor grid. Fluidization is effected in the bottom portion of the bed by flowing feed upward of the grid. Process conditions in the reactor can be controlled within the specified dehydrocyclization ranges, e.g., by one or more of adjusting feed temperature, catalyst temperature, catalyst circulation rate, and by an indirect transfer of heat to or from the bed.

The specified average catalyst particle residence time in the reaction zone is achieved by withdrawing catalyst from above a grid. The withdrawn catalyst is passed to a regeneration vessel where combustible deposits (e.g., coke) are removed by oxidation with air or other regeneration media. Should the combustion of these deposits provide insufficient heat to maintain the dehydrocyclization reaction in thermal balance, additional heat may be added via additional direct or indirect heat transfer. Alternatively or in addition, further catalyst heating during regeneration can be used, e.g., exposing the catalyst to heated vapor (such as heated nitrogen, heated oxygen, heated air, etc.) and/or combusting a flue gas or other fuel stream in the regenerator, provided the catalyst does not exceed the temperature at which catalyst de-alumination and/or loss of structure would occur. Regenerated catalyst is returned to the reactor. To maintain the reactor's fluidized bed in mass balance, the mass of the withdrawn catalyst is typically substantially the same as that of the replacement catalyst.

A product comprising the desired aromatic hydrocarbon, e.g., BTX, can be conducted to a product separation stage for separating at least a portion of the product's aromatic hydrocarbon and optionally at least a portion of the product's non-aromatics. Non-aromatics can be recycled to the process, e.g., as feed and/or fuel components.

qThe dehydrocyclization catalyst in the reactor can have the form of a plurality of catalyst particles located in a turbulent bed. Typically, the bed has a density in the range of from 100 kg/m$^3$ to 500 kg/m$^3$ and a superficial fluid velocity in the range of 0.1 m/s to 10 m/s, such as 0.3 m/s to 2 m/s. Size distribution of the dehydrocyclization catalyst is selected so that the catalyst will mix well throughout the bed. Large particles, e.g., those having a particle size greater than 250 μm, are generally avoided. Typically, ≥50 wt. % of the catalyst is in a particle size range of from about 1 μm to 150 μm, e.g., ≥75 wt., or ≥90 wt. The dehydrocyclization typically has an average particle size in the range of about 20 μm to about 100 μm, e.g., 40 μm to 80 μm. It is also typical for the catalyst to have an average density in the range of from 0.6 g/cm$^3$ to 2 g/cm$^3$. The catalyst circulation rate is selected to achieve an average residence time for the dehydrocyclization catalyst in the reactor's catalyst bed that is ≤90 seconds, e.g., ≤60 seconds, such as ≤30 seconds, or ≤10 seconds, or ≤1 second, or in the range of from 0.1 seconds to 10 seconds. For an appropriately-sized reactor vessel having a bed of volume $V_B$ of fluidized dehydrocyclization catalyst, the circulation rate can be adjusted in the desired range using valve means in fluidic communication with the reactor and regenerator vessels. Typically, fresh or freshly-regenerated catalyst is added to the process to replace catalyst and/or catalyst fines removed from the process, e.g., during product recovery. This is an aid in maintaining $V_B$ substantially constant. In certain aspects, the dehydrocyclization catalyst is removed from (and added to) the fluid bed of reactor 10 at a rate ≥0.11 $V_B$/second, e.g., ≥0.017 $V_B$/second, such as ≥0.033 $V_B$/second, or ≥0.1 $V_B$/second, or ≥1 $V_B$/second, or in the range of from 0.03 $V_B$/second to 100 $V_B$/second, or 0.1 $V_B$/second to 10 $V_B$/second. Those skilled in the art will appreciate that riser reactors such as those used for carrying out fluidized catalytic cracking reactions may be an appropriate form of fluidized catalyst reactor when the catalyst particle residence time in the reaction zone is of relatively short duration, e.g., in the range of from 0.010 second to 0.1 second (equivalent to 10 $V_B$/second to 100 $V_B$/second). Typically, ≥90 wt. % of the replacement catalyst particles comprise regenerated catalyst particles. It is also typical for the freshly regenerated catalyst particles to be at a greater temperature than the equilibrium dehydrocyclization catalyst in the fluid bed of the reactor, but in other respects to have substantially the same physical, chemical, and compositional properties. The invention is not limited to aspects having one fluidized bed for carrying out the dehydrocyclization and one fluidized bed for carrying out the regeneration. Fluidized bed reactors systems having a plurality of fluidized beds for carrying out one or more of the specified dehydrocyclization reactions and/or one or more of the specified regenerations are within the scope of the invention, including those having a plurality of reactor and/or regenerator vessels. In particular, the dehydrocyclization is carried out in a staged fluidized bed reactor.

Particular aspects of the invention are disclosed in the following numbered paragraphs. The invention is not limited to these aspects and this description is not meant to foreclose other aspects within the broader scope of the invention.

Paragraph 1. A catalyst comprising:
  (a) a crystalline aluminosilicate having a Constraint Index in the range of 1 to 12;
  (b) a first metal; and
  (c) at least one selectivating agent selected from the group consisting of an organo-aluminate, an organo-phosphate, and mixtures thereof.

Paragraph 2. The catalyst of Paragraph 1, further comprising a second metal, wherein said second metal is different from said first metal.

Paragraph 3. A catalyst comprising:
  (a) a crystalline aluminosilicate having a Constraint Index in the range of 1 to 12;
  (b) a first metal and a second metal, wherein said second metal is different from said first metal; and
  (c) at least one organo-silicate selectivating agent.

Paragraph 4. The catalyst of Paragraph 3, wherein said second metal is selected from the group consisting of lanthanum, rhenium, silver, palladium, tin, molybdenum, and mixtures of two or more thereof.

Paragraph 5. The catalyst of Paragraph 3 or Paragraph 4, wherein said second metal is lanthanum.

Paragraph 6. The catalyst of any one of Paragraphs 3 to 5, wherein said catalyst has from about 0.005 wt. % to about 1.5 wt. % of said second metal, based on the weight of said catalyst.

Paragraph 7. The catalyst of any one of Paragraphs 3 to 6, wherein said organo-silicate selectivating agent is a tetraalkyl orthosilicate selected from the group consisting of a tetramethyl orthosilicate (TMOS), a tetraethyl orthosilicate (TEOS), a tetrapropyl orthosilicate (TPOS), and mixtures of two or more thereof.

Paragraph 8. The catalyst of any preceding Paragraph, wherein said crystalline aluminosilicate zeolite has a Constraint Index of 1 to 12 is selected from the group consisting of a MCM-22 family material, ZSM-5, ZSM-11, ZSM-12, ZSM-21, ZSM-22, ZSM-23, ZSM-35, ZSM-38, ZSM-48, ZSM-50, ZSM-57, MCM-68, and mixtures of two or more thereof.

Paragraph 9. The catalyst of any preceding Paragraph wherein said crystalline aluminosilicate zeolite which has a Constraint Index of 1 to 12 is ZSM-5.

Paragraph 10. The catalyst of any preceding Paragraph, wherein said first metal is selected from the group consisting of zinc, gallium, platinum, copper, rhenium, iron, and mixtures of two or more thereof.

Paragraph 11. The catalyst of any preceding Paragraph, wherein said first metal is zinc.

Paragraph 12. The catalyst of any preceding Paragraph, wherein said selectivating agent is tetraethylorthosilicate (TEOS).

Paragraph 13. The catalyst of any preceding Paragraph, wherein said catalyst aluminosilicate has from about 0.005 wt. % to about 1.5 wt. % of said first metal, based on the weight of said catalyst.

Paragraph 14. The catalyst of any preceding Paragraph, wherein said catalyst aluminosilicate has at least about 0.005 wt. % of said selectivating agent, based on the weight of said catalyst.

Paragraph 15. The catalyst of any preceding Paragraph, wherein said catalyst has over about 40% reaction selectivity to single-ring aromatic hydrocarbons, in a process for conversion of a light paraffinic hydrocarbon feedstock comprising one or more light hydrocarbons having no more than five carbon atoms to form a product comprising at least one single-ring aromatic hydrocarbon under conversion conditions which include at least a temperature in the range of about 450° C. to about 750° C., a pressure in the range of from about 35 kPa to about 1480 kPa and a WHSV from about 0.1 to about 20 hr$^{-1}$.

Paragraph 16. The catalyst of Paragraph 15, wherein said single-ring aromatic hydrocarbon is selected from the group consisting of benzene, toluene and xylene, and mixtures of two or more thereof.

Paragraph 17. The catalyst of any preceding Paragraph, wherein said catalyst has less than about 10% reaction selectivity to multiple-ring aromatic compounds, in a process for conversion of a light paraffinic hydrocarbon feedstock comprising one or more light hydrocarbons having no more than five carbon atoms to single-ring aromatic hydrocarbons under conversion conditions which include at least a temperature in the range of about 450° C. to about 750° C., a pressure in the range of from about 35 kPa to about 1480 kPa and a WHSV from about 0.1 to about 20 hr$^{-1}$.

Paragraph 18. The catalyst of Paragraph 17, wherein said multiple-ring compound is naphthalene.

Paragraph 19. A selectivated catalyst comprising:
  (a) ZSM-5 or ZSM-11;
  (b) about 0.005 wt. % to about 1.5 wt. % of zinc, based on the weight of said selectivated catalyst; and
  (c) at least about 0.005 wt. % of a tetraalkyl orthosilicate selectivating agent, based on the weight of said selectivated catalyst, said tetraalkyl orthosilicate selectivating agent is selected from the group consisting of a tetramethyl orthosilicate (TMOS), a tetraethyl orthosilicate (TEOS), a tetrapropyl orthosilicate (TPOS), and mixtures of two or more thereof,
  wherein said selectivated catalyst provides over about 40% reaction selectivity to benzene, toluene or xylenes, and mixtures thereof, and/or less than about 10% reaction selectivity to naphthalene, in the process for conversion of a light paraffinic hydrocarbon feedstock comprising one or more light hydrocarbons having no more than five carbon atoms to form a product comprising at least one single-ring aromatic hydrocarbon under conversion conditions which include at least a temperature in the range of about 450° C. to about 750° C., a pressure in the range of from about 35 kPa to about 1480 kPa and a WHSV from about 0.1 to about 20 hr$^{-1}$.

Paragraph 20. The selectivated catalyst of Paragraph 19, further comprising:
  (d) about 0.005 to about 1.5 wt. % of lanthanum, based on the weight of said selectivated catalyst.

Paragraph 21. The catalyst or selectivated catalyst of any preceding Paragraph, wherein said crystalline aluminosilicate zeolite is in hydrogen form.

Paragraph 22. The catalyst or selectivated catalyst of any preceding Paragraph, wherein said catalyst or selectivated catalyst further comprises a binder selected from the group consisting of alumina, silica, clay, titania, zirconia and a mixture of two or more thereof.

Paragraph 23. A method of making a selectivated catalyst comprising the steps of:

(a) providing a crystalline aluminosilicate comprising ZSM-5 or ZSM-11 which optionally has hydrogen ions;

(b) contacting said crystalline aluminosilicate with a source of a first metal and optionally a source of a second metal under conditions effective to deposit said first metal and said optional second metal on said crystalline aluminosilicate and form a metal-containing crystalline aluminosilicate, wherein said first metal is different from said second metal, said first metal is selected from the group consisting of zinc, gallium, platinum, copper, rhenium, iron, and mixtures of two or more thereof, and said second metal is selected from the group consisting of lanthanum, rhenium, silver, palladium, tin, molybdenum, and mixtures of two or more thereof; and (c) selectivating said metal-containing crystalline aluminosilicate of step (b) by contacting with a selectivating agent under conditions effective to deposit said selectivating agent on said metal-containing crystalline aluminosilicate and form said selectivated catalyst, wherein said selectivating agent is a tetraalkyl orthosilicate selected from the group consisting of a tetramethyl orthosilicate (TMOS), a tetraethyl orthosilicate (TEOS), a tetrapropyl orthosilicate (TPOS), and mixtures of two or more thereof.

Paragraph 24. The method of Paragraph 23, wherein said selectivating step (c) is performed before said contacting step (b).

Paragraph 25. The method of Paragraph 23 or Paragraph 24, which further comprises the step:

(d) calcining said selectivated catalyst at a temperature of about 550° C. for 1 or more hours.

Paragraph 26. The method of any one of Paragraphs 23 to 25, wherein said first metal is zinc and said source of zinc is selected from the group consisting of zinc nitrate, zinc titanate, zinc silicate, zinc borate, zinc fluorosilicate, zinc fluorotitanate, zinc molybdate, zinc chromate, zinc tungstate, zinc zirconate, zinc chromite, zinc aluminate, zinc phosphate, zinc acetate dihydrate, diethyl zinc, zinc 2-ethylhexanoate, and mixtures of two or more thereof.

Paragraph 27. The method of any one of Paragraphs 23 to 26, wherein said second metal is lanthanum and said source of lanthanum is a lanthanum salt, a lanthanum nitrate, or a mixture thereof.

Paragraph 28. A process for conversion of a light paraffinic hydrocarbon feedstock comprising one or more light hydrocarbons having no more than five carbon atoms to form a product comprising at least one single-ring aromatic hydrocarbon having six or more carbon atoms, the process comprising the step of contacting said feedstock under suitable conversion conditions in the presence of a catalyst of any one of Paragraphs 1 to 22 or made by the method of any one of Paragraphs 23 to 27, to form said product.

Paragraph 29. The process of Paragraph 28, wherein said one or more light hydrocarbons is selected from the group consisting of methane, ethane, propane, butane, and mixtures of two or more thereof.

Paragraph 30. The process of Paragraph 28 or Paragraph 29, wherein said single-ring aromatic hydrocarbon is selected from the group consisting of benzene, toluene, xylenes, and mixtures of two or more thereof.

Paragraph 31. The process of any one of Paragraphs 28 to 30, wherein said suitable conversion conditions include at least a temperature of in the range of about 450° C. to about 750° C., a pressure in the range of from about 35 kPa to about 1480 kPa and a WHSV from about 0.1 to about 20 $hr^{-1}$.

Paragraph 32. The process of any one of Paragraphs 28 to 31, wherein said catalyst provides over about 40% reaction selectivity to benzene, toluene or xylenes, and mixtures thereof, and/or less than about 10% reaction selectivity to naphthalene, in the process for conversion of a light paraffinic hydrocarbon feedstock comprising one or more light hydrocarbons having no more than five carbon atoms to form a product comprising at least one single-ring aromatic hydrocarbon under said suitable conversion conditions.

EXAMPLES

The invention will now be more particularly described with reference to the following Examples. Numerous modifications and variations are possible and it is to be understood that within the scope of the appended claims, the invention may be practiced otherwise than as specifically described herein.

Alpha Value

The alpha value is a measure of the cracking activity of a catalyst and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

Materials

H-ZSM-5 was used as the starting material to synthesize the catalysts of the Examples. The Alpha value for the H-ZSM-5 was 440. As used in the Examples, the percentages of metal, i.e., zinc, Zn, and lanthanum, La, are in weight percent, which is based on the weight of the catalyst.

Example 1—1% Zn/ZSM-5

Seventy (70) grams of the H-ZSM-5 sieve (or grinded bound H-ZSM-5 sieve) is dispersed in 400 ml of a solution of Zinc-nitrate (3% of $Zn(NO_3)_2$—Zn-nitrate 99%, as purchased from Fluka) and stirred for 4 hr at room temperature. The solid was recovered and dried at 120° C. for 16 hr.

Example 2—0.5% La-1% Zn/ZSM-5

Seventy (70) grams of the H-ZSM-5 sieve was dispersed in 400 ml of a solution of Zinc-nitrate (3% of $Zn(NO_3)_2$—Zn-nitrate 99%, as purchased from Fluka) and stirred for 4 hr at room temperature. The solid was recovered and dried at 120° C. for 16 hrs. Thirty-five (35) grams of dried material was then dispersed in 200 ml of a Lanthanum-nitrate solution (1% of $La(NO_3)_3$—La-nitrate 99.9%, as purchased from Aldrich) and stirred for 4 hrs. The solid was recovered and dried at 120° C. for 16 hrs.

Tetraethylorthosilicate (TEOS) Treatment for Examples 3 to 6

Twenty (20) grams of the Zn/ZSM-5 or La/ZSM-5 or grinded H-ZSM-5 molecular sieves were treated in 100 g of tetraethylorthosilicate (TEOS, 98%, purchased from Aldrich) at room temperature under agitation in a closed polyethylene (PE) bottle. After treatment, the TEOS was decanted, the molecular sieve material was dried and calcined in air according to the following program: 1.7° C./min to 120° C. and hold for 16 hr
3.3° C./min to 550° C. for 6 hr; and 5° C./min to 50° C.

Example 3—TEOS-1% Zn/ZSM-5

The 1% Zn-ZSM-5 catalyst of Example 1 was subjected to the TEOS treatment (described above) to obtain the TEOS-1% Zn-ZSM-5.

Example 4—1% Zn-TEOS/ZSM-5

The H-ZSM-5 was subjected to the TEOS treatment (described above). The resulting TEOS/H-ZSM-5 material was impregnated with 1% Zn using the same procedure for Zn addition to prepare the 1% Zn-ZSM-5 catalyst of Example 1, as described above.

Example 5—TEOS-0.5% La-1% Zn-ZSM-5

The 0.5% La-1% Zn/ZSM-5 catalyst of Example 2 was subjected to the TEOS treatment (described above) to obtain TEOS-0.5% La-1% Zn-ZSM-5.

Example 6—0.5% La-1% Zn-TEOS-ZSM-5

The H-ZSM-5 was subjected to the TEOS treatment (described above). The resulting TEOS/H-ZSM-5 material was impregnated with 0.5% La and 1% Zn using the same procedure for La and Zn addition as 0.5% La-1% Zn-ZSM-5 catalyst of Example 2, described above.

Example 7—Performance Evaluation-Ethane Conversion and Hydrocarbon Selectivity

The catalysts of Example 1 (unselectivated 1% Zn/ZSM-5), Example 3 TEOS selectivated 1% Zn/ZSM-5) and Example 4 (1% Zn on TEOS selectivated ZSM-5) were evaluated for ethane conversion and hydrocarbon selectivity at 600° C., 15 psig (103.4 kPa gauge) pressure, and 0.5 hr$^{-1}$ weight hourly space velocity based on the weight of ethane and the mass of catalyst used. The ethane conversion and hydrocarbon selectivity are reported in Table 2A and Table 2B, below.

As can be seen in Table 2A and Table 2B, the naphthalene selectivity decreases from nearly 12 wt. % for 1% Zn/ZSM-5 catalyst, and to about 4 wt. % for TEOS-1% Zn/ZSM-5 catalyst, and to about 2 wt. % for 1% Zn-TEOS/ZSM-5 catalyst. The single-ring aromatic hydrocarbon A9-11 selectivity increases from 44 wt. % for Zn-ZSM-5 catalyst to 49 wt. % for TEOS-Zn-ZSM-5 catalyst. This comes at the loss of activity (measured by ethane conversion) from about 47% for 1% Zn-ZSM-5 catalyst to about 43% for TEOS-1% Zn-ZSM-5 catalyst. The methane, olefins and paraffins selectivity are similar for 1% Zn-ZSM-5 catalyst and TEOS-1% Zn-ZS M-5 catalyst.

Table 2B shows that the TEOS-1% Zn-ZSM-5 catalyst has higher benzene, toluene, and single-ring aromatic hydrocarbons A9-11 selectivities, but lower xylenes selectivities as compared to 1% Zn-ZSM-5 catalyst. On the other hand, 1% Zn-TEOS-ZSM-5 catalyst of Example 4 results in substantially lower conversion (about 24 wt. %) and single-ring aromatic hydrocarbon A9-11 selectivity (less than about 0.7 wt. %).

TABLE 2A

Ethane Conversion and Hydrocarbon Selectivity over TEOS Selectivated and Unselectivated Zn/ZSM-5 Catalysts at 600° C., 5 hr–$^{1}$ and Less Than 5 Minutes Time On Stream

| | | Hydrocarbon Selectivity, wt. % | | | | |
|---|---|---|---|---|---|---|
| Example | Ethane Conversion | Paraffins | Olefins | Single-Ring Aromatic Hydrocarbon A9-11 | Naphthalene | Methane |
| 1 1% Zn/ZSM-5 | 46.57 | 3.89 | 11.11 | 44.01 | 11.97 | 29.02 |
| 3 TEOS- 1% Zn/ZSM-5 | 42.70 | 2.74 | 13.54 | 49.06 | 3.93 | 30.70 |
| 4 1% Zn- TEOS/ZSM-5 | 33.46 | 3.47 | 21.73 | 34.37 | 1.99 | 38.36 |

TABLE 2B

Aromatics Selectivity over TEOS Selectivated and Unselectivated Zn/ZSM-5 Catalysts at 600° C., 5 hr$^{-1}$ And Less Than 5 Minutes Time On Stream

| | Hydrocarbon Selectivity, wt. % | | | |
|---|---|---|---|---|
| Example | Benzene | Toluene | Xylenes | Single-Ring Aromatic Hydrocarbon A9-11 |
| 1 1% Zn/ZSM-5 | 22.00 | 16.84 | 3.45 | 1.40 |
| 3 TEOS-1% Zn/ZSM-5 | 26.38 | 19.95 | 0.78 | 1.56 |
| 4 1% Zn-TEOS/ZSM-5 | 19.71 | 13.59 | 0.06 | 0.67 |

Example 8—Performance Evaluation-Ethane Conversion and Hydrocarbon Selectivity

The catalysts of Example 2 (unselectivated 0.5% La-1% Zn/ZSM-5), Example 5 TEOS selectivated 0.5% La-1% Zn/ZSM-5) and Example 6 (0.5% La-1% Zn on TEOS selectivated ZSM-5) were evaluated for ethane conversion and hydrocarbon selectivity at 600° C., 15 psig (103.4 kPa gauge) pressure, and 0.5 hr$^{-1}$ weight hourly space velocity based on the weight of ethane and the mass of catalyst used. The ethane conversion and hydrocarbon selectivity are reported in Table 3, below.

Table 3 shows ethane conversion for TEOS selectivated and un-selectivated 0.5% La-1% Zn-ZSM-5 catalysts that are similar to those reported in Table 2A and Table 2B. Again, TEOS-0.5% La-1% Zn-ZSM-5 catalyst shows higher single-ring aromatic hydrocarbon A9-11 selectivity of about 51 wt. % as compared to about 43 wt. % for 0.5% La-1% Zn-ZSM-5 catalyst. Lower naphthalene selectivity, 1.3 wt. % for TEOS-0.5% La-1% Zn-ZSM-5 catalyst as compared to 13.16 wt. % for 0.5% La-1% Zn-ZSM-5 catalyst. Lower activity (as measured by ethane conversion) of about 42 wt. % TEOS-0.5% La-1% Zn-ZSM-5 catalyst as compared to about 47 wt./% for unselectivated 0.5% La-1% Zn-ZSM5 catalyst.

TABLE 3

Ethane Conversion and Hydrocarbon Selectivity over TEOS Selectivated and Unselectivated La/ZSM-5 Catalysts at 600° C., 5 hr$^{-1}$ and less than 5 minutes Time on Stream

| Example | Ethane Conversion | Hydrocarbon Selectivity, wt. % | | | | |
| --- | --- | --- | --- | --- | --- | --- |
| | | Paraffins | Olefins | Single-Ring Aromatic Hydrocarbon A9-11 | Naphthalene | Methane |
| 2 0.5% La-1% Zn/ZSM-5 | 46.52 | 1.69 | 11.19 | 43.45 | 13.16 | 30.49 |
| 5 TEOS-0.5% La-1% Zn/ZSM-5 | 41.61 | 2.28 | 14.51 | 51.17 | 1.30 | 30.72 |
| 6 0.5% La-1% Zn-TEOS/ZSM-5 | 38.06 | 2.70 | 18.08 | 41.29 | 5.64 | 32.27 |

Example 9—Performance Evaluation-Propane Conversion

The catalysts of Example 2 (unselectivated 0.5% La-1% Zn/ZSM-5), Example 5 TEOS selectivated 0.5% La-1% Zn/ZSM-5) and Example 6 (0.5% La-1% Zn on TEOS selectivated ZSM-5) were further evaluated for propane conversion and hydrocarbon selectivity at 600° C., 15 psig (103.4 kPa gauge) pressure, and 0.5 hr$^{-1}$ weight hourly space velocity based on the weight of propane and the mass of catalyst used. The ethane conversion and hydrocarbon selectivity are reported in Table 4, below.

Table 4 shows propane conversion for TEOS selectivated and un-selectivated 0.5% La-1% Zn-ZSM-5 catalysts are similar to those reported in Table 2 for ethane conversion.

TABLE 4

Propane Conversion and Hydrocarbon Selectivity over TEOS Selectivated and Unselectivated La/ZSM-5 Catalysts at 600° C., 0.5 hr$^{-1}$ and less than 5 minutes Time on Stream

| Example | Propane Conversion | Hydrocarbon Selectivity, % | | | | |
| --- | --- | --- | --- | --- | --- | --- |
| | | Paraffins | Olefins | Single-Ring Aromatic Hydrocarbon A9-11 | Naphthalene | Methane |
| 2 0.5% La-1% Zn/ZSM-5 | 98.27 | 25.52 | 2.26 | 43.59 | 6.90 | 21.73 |
| 5 TEOS-0.5% La-1% Zn/ZSM-5 | 98.48 | 26.21 | 2.22 | 44.90 | 5.52 | 21.13 |
| 6 0.5% La-1% Zn-TEOS/ZSM-5 | 92.77 | 26.56 | 5.85 | 40.96 | 2.76 | 23.85 |

As the experimental data shows above, selectivation, especially TEOS selectivation, after metal addition, as compare to adding metals after selectivating H-ZSM-5 with TEOS results in the most favorable yield slate; namely, an increase in benzene, toluene, xylenes (BTX) selectivities, a reduced naphthalene selectivity, and a small decrease in feed conversion.

While the experimental data shows that selectivation can be effectively used to increase BTX, reduce naphthalene produced over Zn-ZSM-5 and La—Zn-ZSM-5 catalysts, a similar effect can be achieved over other catalysts such as Ga-ZSM-5, Pt-ZSM-5, Fe-ZSM-5, and other variations, such as Cu-ZSM-5 and Rh-ZSM-5.

Further, while the experimental data shows that selectivation can be effectively used to increase BTX, reduce naphthalene for ethane and light alkanes (e.g., light paraffinic hydrocarbon) as feedstock, a similar effect can be achieved over feedstock, such as, for example, pentane, iso-pentane, methanol, $C_2$-$C_5$ olefins.

Certain embodiments and features have been described using a set of numerical upper limits and a set of numerical lower limits. When numerical lower limits and numerical upper limits are listed herein, ranges from any lower limit to any upper limit are contemplated, and are expressly within the scope of the invention. Certain lower limits, upper limits and ranges appear in one or more claims below. All numerical values take into account experimental error and variations that would be expected by a person having ordinary skill in the art. The term "comprising" is synonymous with the term "including". Likewise whenever a composition, an element or a group of components is preceded with the transitional phrase "comprising", it is understood that we also contemplate the same composition or group of components with transitional phrases "consisting essentially of," "consisting of", "selected from the group of consisting of,"

or "is" preceding the recitation of the composition, component, or components, and vice versa.

Various terms have been defined above. To the extent a term used in a claim is not defined above, it should be given the broadest definition persons in the pertinent art have given that term as reflected in at least one printed publication or issued patent. Furthermore, all patents, patent applications, any test procedures, and other documents cited in this application are fully incorporated by reference in their entirety to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The invention claimed is:

1. A process for conversion of a light paraffinic hydrocarbon feedstock comprising one or more light hydrocarbons having no more than five carbon atoms, the one or more light hydrocarbons comprising ethane, to form a product comprising at least one single-ring aromatic hydrocarbon having six or more carbon atoms, said process comprising the step of contacting said feedstock under suitable conversion conditions in the presence of a catalyst which includes
(a) a crystalline aluminosilicate having a Constraint Index in the range of 1 to 12;
(b) a first metal and a second metal, wherein said second metal is different from said first metal; and
(c) at least one organo-silicate selectivating agent,
wherein the catalyst comprises at least 0.005 wt. % of the selectivating agent, based on a weight of the catalyst, the selectivating agent being added to the catalyst after addition of the first metal and the second metal.

2. The process of claim 1, wherein said one or more light hydrocarbons further comprise methane, propane, butane, and mixtures of two or more thereof.

3. The process of claim 1, wherein said single-ring aromatic hydrocarbon is selected from the group consisting of benzene, toluene, xylenes, and mixtures of two or more thereof.

4. The process of claim 1, wherein said suitable conversion conditions include at least a temperature of in the range of about 450° C. to about 750° C., a pressure in the range of from about 35 kPa to about 1480 kPa and a WHSV from about 0.1 $hr^{-1}$ to about 20 $hr^{-1}$.

5. The process of claim 4, wherein said catalyst provides over about 40% reaction selectivity to benzene, toluene or xylenes, and mixtures thereof, and/or less than about 10% reaction selectivity to naphthalene, in a process for conversion of a light paraffinic hydrocarbon feedstock comprising one or more light hydrocarbons having no more than five carbon atoms to form a product comprising at least one single-ring aromatic hydrocarbon under said suitable conversion conditions.

6. The process of claim 1, wherein the first metal is selected from the group consisting of zinc, gallium, platinum, copper, rhenium, iron, and mixtures of two or more thereof.

* * * * *